United States Patent

(12) United States Patent
Gobbi Frattini

(10) Patent No.: US 12,097,168 B2
(45) Date of Patent: Sep. 24, 2024

(54) STERILE AND STERILIZED PACKAGE FOR ADMINISTRATION OF MEDICINAL OR NUTRITIONAL SUBSTANCES

(71) Applicant: ADIENNE Pharma & Biotech SA, Lugano (CH)

(72) Inventor: Paolo Giuseppe Gobbi Frattini, Sondalo So (IT)

(73) Assignee: ADIENNE Pharma & Biotech SA, Lugano (CH)

( * ) Notice: Subject to any disclaimer, the term of this patent is extended or adjusted under 35 U.S.C. 154(b) by 0 days.

(21) Appl. No.: 16/799,950

(22) Filed: Feb. 25, 2020

(65) Prior Publication Data

US 2020/0268607 A1    Aug. 27, 2020

(30) Foreign Application Priority Data

Feb. 26, 2019    (IT) .......................... 102019000002745

(51) Int. Cl.
 *A61J 1/14* (2023.01)
 *A61J 1/10* (2006.01)
 *A61J 1/20* (2006.01)

(52) U.S. Cl.
 CPC .............. *A61J 1/1468* (2015.05); *A61J 1/10* (2013.01); *A61J 1/1406* (2013.01); *A61J 1/145* (2015.05);
 (Continued)

(58) Field of Classification Search
 CPC .......... A61J 1/1468; A61J 1/145; A61J 1/201; A61J 1/2051; A61J 1/10; A61J 1/1406;
 (Continued)

(56) References Cited

U.S. PATENT DOCUMENTS 4,834,152 A * 5/1989 Howson ................ A61M 5/162
                                                       604/416
5,779,693 A * 7/1998 Ropiak ................. A61J 1/1487
                                                       604/408
(Continued)

FOREIGN PATENT DOCUMENTS

EP    0225861    6/1987
EP    0426403    5/1991
(Continued)

OTHER PUBLICATIONS

Italian Search Report.
(Continued)

*Primary Examiner* — Kai H Weng
*Assistant Examiner* — Alessandro R Del Priore
(74) *Attorney, Agent, or Firm* — Sterne, Kessler, Goldstein & Fox P.L.L.C.

(57) ABSTRACT

A package for administration of fluid medicinal or nutritional substances features an outer bag with a sterile or sterilized inner chamber and inside chamber a bottle of medicinal or nutritional substance with a neck, a pierceable cap and a device for the withdrawal and/or reconstitution of the substance, placed below the cap of the bottle. The device comprises a perforation needle axially movable to the bottle and an outflow tube extending out of the bag equipped with an openable closure. The perforation needle is crossed longitudinally by a first channel connecting with the closure set open to the outflow tube, and a second channel with a side opening equipped with a hydrophobic filter configured to allow, after perforation of the cap, only air or other gaseous fluids to flow from inside the bottle into the inner chamber of the bag or vice versa.

10 Claims, 9 Drawing Sheets

(52) U.S. Cl.
CPC ............. *A61J 1/201* (2015.05); *A61J 1/2051* (2015.05); *A61J 1/2089* (2013.01); *A61J 1/2096* (2013.01)

(58) Field of Classification Search
CPC ...... A61J 1/2089; A61J 1/2096; A61J 1/1481; A61J 1/20; A61J 1/14; A61J 1/05; A61J 1/1412; A61J 1/2082; A61J 1/2048; A61J 1/12; A61J 1/1475; A61J 1/2058; A61J 1/2075; A61J 1/2093; A61J 1/1443; A61M 2039/1061; A61M 5/14; B65D 81/32; B65D 81/3216; A61L 2/202; A61L 2/0094; A61L 2202/23

See application file for complete search history.

(56) References Cited

U.S. PATENT DOCUMENTS

| | | | |
|---|---|---|---|
| 6,464,105 B1* | 10/2002 | Rolle | A61J 1/2096 222/459 |
| 2001/0029360 A1* | 10/2001 | Miyoshi | A61J 1/2096 604/533 |
| 2007/0079894 A1* | 4/2007 | Kraus | A61J 1/201 141/319 |
| 2007/0088252 A1* | 4/2007 | Pestotnik | B01F 35/75425 604/82 |
| 2008/0172024 A1* | 7/2008 | Yow | A61J 1/2096 604/411 |
| 2011/0178493 A1* | 7/2011 | Okiyama | A61J 1/2096 604/407 |
| 2013/0033034 A1* | 2/2013 | Trombley, III | A61M 5/007 285/132.1 |
| 2013/0225903 A1* | 8/2013 | Franci | A61N 5/1007 600/4 |
| 2015/0083950 A1 | 3/2015 | Okiyama | |
| 2016/0000650 A1* | 1/2016 | Gobbi Frattini | B65D 81/3216 604/408 |
| 2016/0000653 A1 | 1/2016 | Kramer | |
| 2017/0100307 A1* | 4/2017 | Gobbi Frattini | A61J 1/2065 |
| 2019/0142695 A1* | 5/2019 | Eli | A61J 1/2096 604/415 |

FOREIGN PATENT DOCUMENTS

| | | |
|---|---|---|
| EP | 2399565 | 12/2011 |
| EP | 2962676 | 1/2016 |
| EP | 3158987 | 4/2017 |
| EP | 3545935 | 10/2019 |
| GB | 2117733 | 10/1983 |
| IT | 202016000058207 | 7/2016 |
| JP | H 0824312 A | 1/1996 |
| JP | 2016-512135 | 4/2016 |
| WO | WO-9926580 A1 | 6/1999 |
| WO | WO 2010061743 | 6/2010 |
| WO | 2011/071952 | 6/2011 |
| WO | WO-2011071952 A2 * | 6/2011 ............ A61J 1/2089 |

OTHER PUBLICATIONS

Eurasian Search Report.
Notice of Reasons for Rejection from counterpart Japanese patent application No. 2020-026303, dated Nov. 7, 2023, and machine translation, 6 pages.
Examination Report from counterpart Indian patent application No. 202024006615, dated Sep. 15, 2023, and machine translation, 5 pages.
First Office Action from counterpart Chinese patent application No. 202010106920.7, dated Sep. 28, 2023, and machine translation, 3 pages.
Office Action for Chilean Patent Application No. 202000409, dated May 28, 2021, National Institute of Industrial Property, Santiago, Chile, 6 pages.
Office Action for Singaporean Patent Application No. 10202001341Q, dated May 3, 2023, Intellectual Property Office of Singapore, Paya Lebar Quarter, Singapore, 12 pages.

* cited by examiner

US 12,097,168 B2

STERILE AND STERILIZED PACKAGE FOR ADMINISTRATION OF MEDICINAL OR NUTRITIONAL SUBSTANCES

BACKGROUND OF THIS INVENTION

The present invention relates to a sterile or sterilized package (that it is sterile from the outset or sterilized at a later stage) for the delivery of medicinal or nutritional substances.

Sterile and sterilized packages suitable for the administration of medicinal or nutritional substances are known. Examples of said packages are disclosed in EP 2962676 B1, EP3158987 B1, EP 3545935 A1, and in the Italian utility model No. 202016000058207.

In said packages, an outer flexible bag with a sterile or sterilized inner chamber houses a bottle of medicinal or nutritional substance with a pierceable cap in an overturned position and an introduction and withdrawal device placed below, equipped with tools for coupling to the cap of the bottle and the perforation of said cap, and with a tube with openable closure extending out of the bag.

Said tube may either be inserted directly into a flexible bag placed below filled with a liquid diluent to be mixed with the substance withdrawn from the bottle (EP 2962676 B1 and EP 3158987 B1) or end with a (male or female) connector, which may be coupled in turn with either a complementary (female or male, respectively) connector of a flexible bag placed below filled with a liquid diluent to be mixed with the substance withdrawn from the bottle, or a syringe for the withdrawal and/or reconstitution of the medicinal or nutritional substance contained in the bottle, or a two-way tap which, depending on its adjustment, connects the connector of the upper bag to a syringe placed on one side of the bag, or said syringe to the connector of a bag placed below, in order to allow the substances in the bottle and lower bag to be mixed in dosed quantities (Italian utility model No. 202016000058207 and EP 3545935 A1).

For all the uses described above the same problem applies, i.e. to keep a difference in pressure between the inside of the bottle—above the level of the liquid contained therein—and the outflow from the tube with the connector open such as to help the substance flow out of the bottle, even without exerting manual pressure from outside on the bag housing the bottle.

SUMMARY OF THE INVENTION

The object of this invention is to address the issue described above in a simple and safe manner, working in a closed system and under sterile conditions and without resorting to measures implying the use of further instrumental devices.

To this purpose, the present invention relates to a package for administration of medicinal or nutritional substances, comprising an outer bag with a sterile or sterilized inner chamber housing a bottle of medicinal or nutritional substance with a pierceable cap in an overturned position, and a device for the withdrawal and/or reconstitution of the substance contained in the bottle, which is placed below the cap of the bottle and may be hooked to the neck of the bottle, said device including a needle for the perforation of the cap of the bottle which is axially movably with respect to the bottle, and an outflow tube with openable closure element extending out of the bag, said package being characterized in that said perforation needle is passed through longitudinally by a first channel connecting—after perforation of the cap and with the closure element set open—the inside of the bottle to said outflow tube, and a second channel with a side opening and a hydrophobic filter configured to allow, after perforation of the cap, only air or other gaseous fluid to flow from inside the bottle into the inner chamber of the bag, or vice versa.

When the needle penetrates through the cap of the bottle and the closure element of the outflow tube is set open, the difference in pressure generated by the structure above triggers the outflow of the medicinal or nutritional substance from the bottle through the tube, and then to the bag or syringe which the tube has been connected to. At this stage, the channel with a side opening equipped with hydrophobic filter ensures the proper air pressure inside the bottle.

DESCRIPTION OF THE DRAWINGS

A possible embodiment and its application possibilities are shown and described—by way of non-limited example—in the appended drawings, in which.

DETAILED DESCRIPTION OF THE INVENTION

Figure 1:
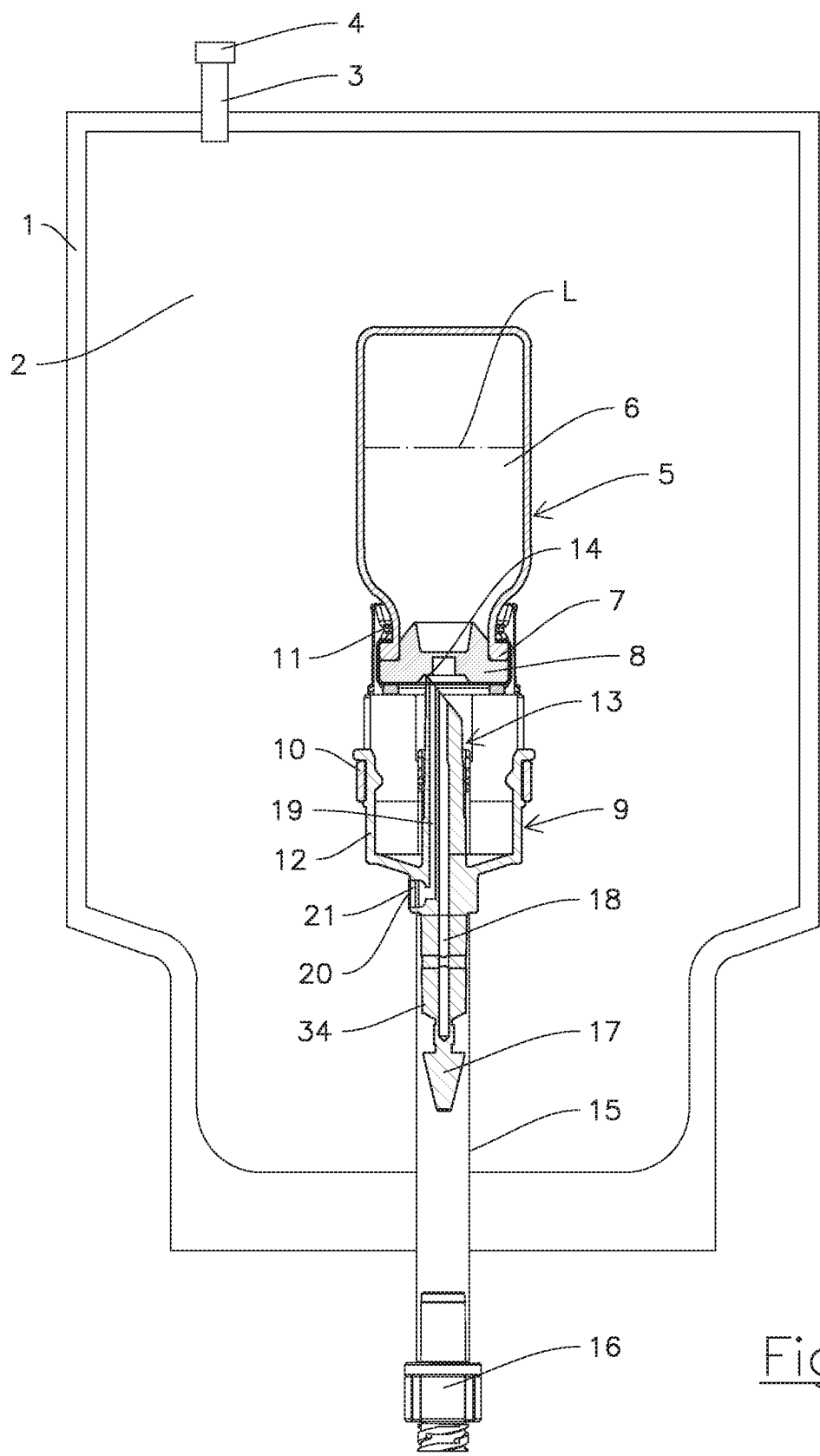
FIG. 1 illustrates a package according to the invention in an initially sealed condition.

The package shown in FIG. 1 features an outer sterile or sterilized flexible bag 1, wherein an inner chamber 2, sterilized for example by means of a mixture of ozone or other sterilizing gas and oxygen delivered through a tube 3 equipped with a connector 4 (for example of the type with an airtight open/close cap as described in EP 2667839 B1), houses and shows an overturned bottle 5 of medicinal or nutritional substance 6 with a neck 7 and a sealed (openable and automatically airtight reasealable) cap 8 in a coupling position, and a withdrawal and/or reconstitution device 9 which is hooked to the neck 7 of the bottle 5 and may be operated from outside bag 1 in order to perforate cap 8 of bottle 5. The dotted line L generically indicates the level of substance 6 inside bottle 5.

Figure 2:
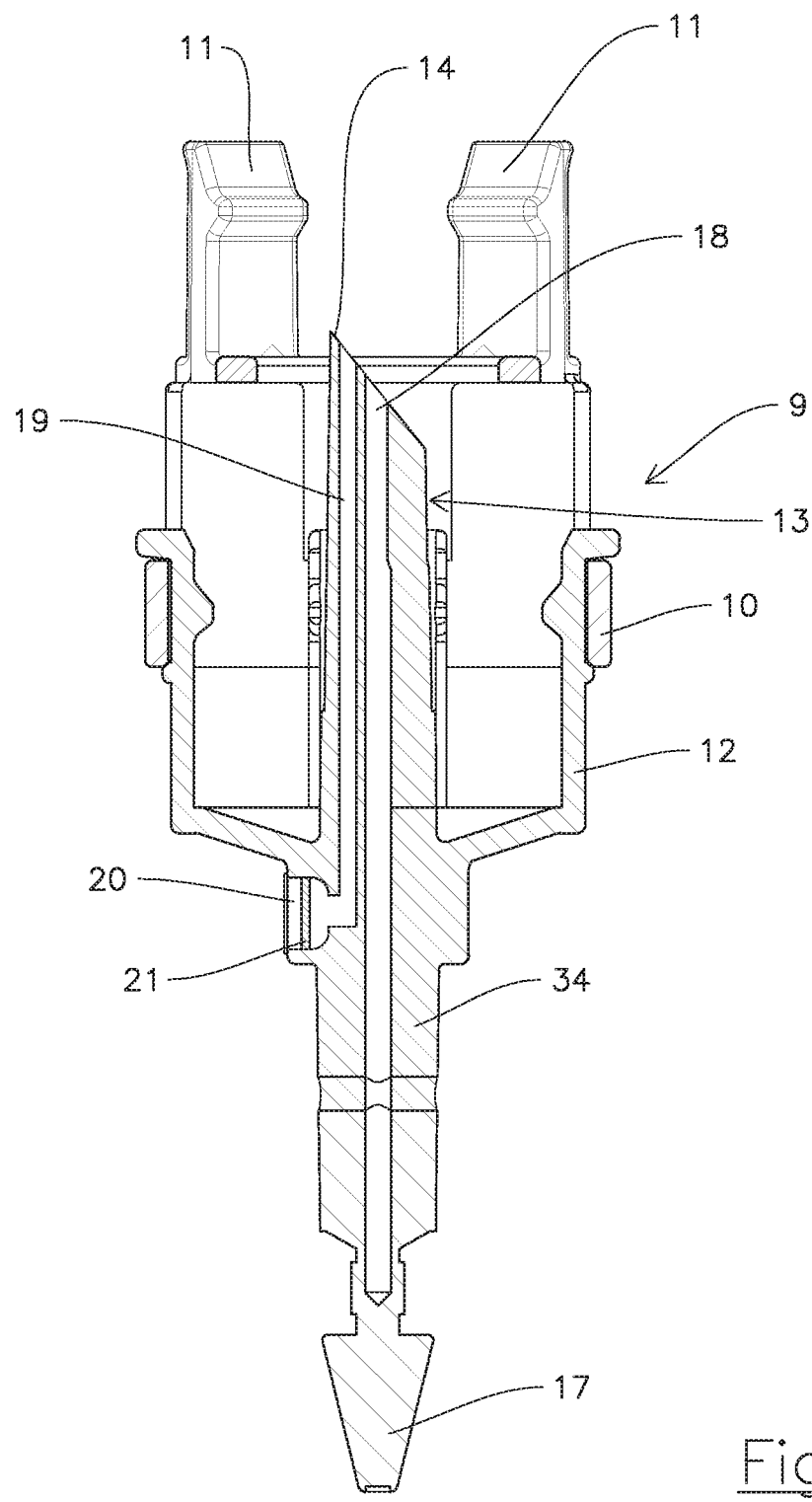
FIG. 2 shows a withdrawal and/or reconstitution device used in the package of FIG. 1 for the coupling and perforation of the cap of a bottle of medicinal or nutritional substance set in an overturned position inside a flexible bag.

FIG. 2 provides a magnified view of device 9 consisting of an upper body 10 equipped with flaps 11 that may be hooked to neck 7 of bottle 5, and a lower body 12 which is coupled to upper body 10 in an axially sliding mode and comprises a perforation needle 13 with a piercing tip 14 protruding upwards and a bottom shank 34 which is hermetically accommodated within a flexible outflow tube 15 ending with an airtight openable and automatically resealable end connector 16 (for example of the type with an airtight open/close cap as described in EP 2667839 B1), and terminates with a frangible closure element 17.

The perforation needle 13 is passed through longitudinally by two channels 18 and 19 running alongside each other, the former being open at the top end and closed at the lower end by the frangible element 17, and the latter being open at the top end and in permanent communication with inner chamber 2 of bag 1 through a side opening 20 equipped with a hydrophobic filter 21 allowing the passage of air or other gaseous fluids, but preventing any liquids from passing through.

In the initial condition described in FIG. 1, with lower body 12 of device 9 set downward from upper body 10 of said device 9, the air or other sterile mixture contained inside inner chamber 2 of bag 1 is left outside bottle 5, which in turn contains medicinal or nutritional substance 6 in a sealed environment.

Figure 3:
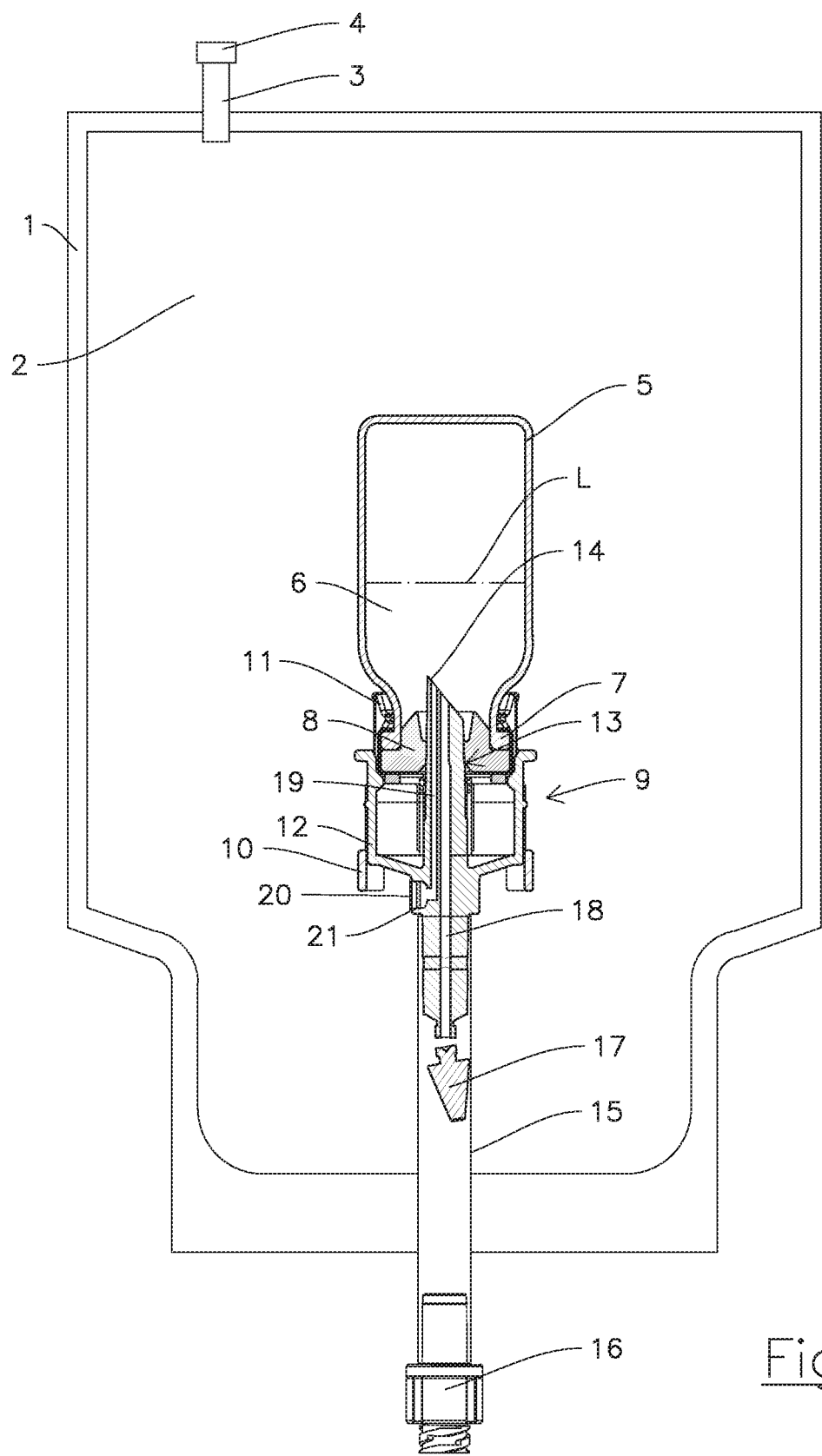
FIG. 3 shows the package of FIG. 1 during administration of the medicinal or nutritional substance.

Pushing bottle 5 down from outside bag 1 towards lower body 12 of device 9, tip 14 of needle 13 perforates cap 8 of bottle 5, whereby channels 18 and 19 are put in communication with the inside of bottle 5, as shown in FIG. 3.

This allows the passage of air or another sterile mixture through hydrophobic filter 21, side opening 20, and up channel 19 till inside bottle 5, forcing medicinal or nutritional substance 6—once the frangible closure 17 is broken—to flow out of bottle 5 and down outflow tube 15 through channel 18 till connector 16, and from there to the external user device (syringe for withdrawal and/or reconstitution, further collection bag or other) by differential pressure. Filter 21 prevents substance 6 from flowing out from the side opening 20.

Figure 4:
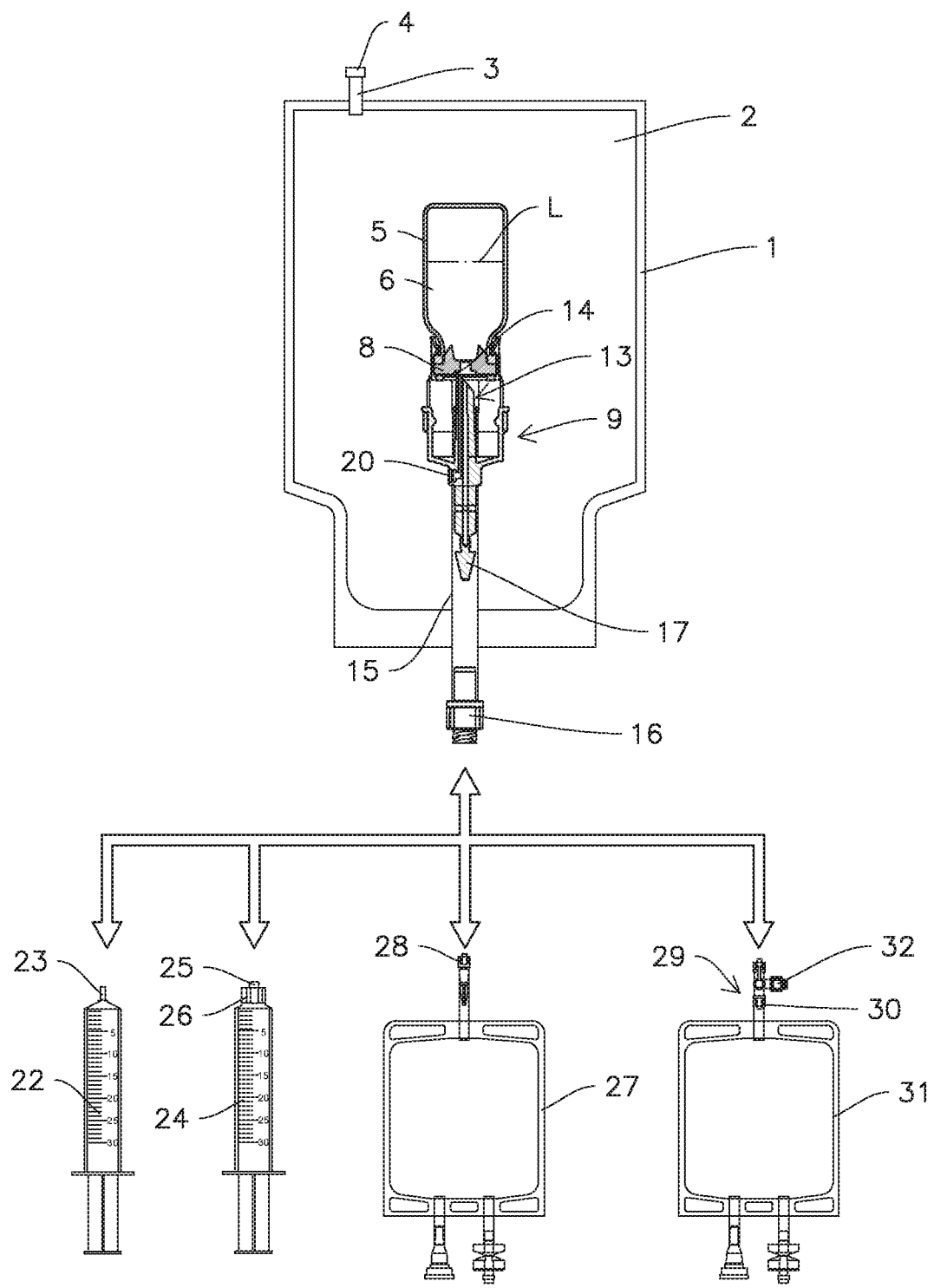
FIG. 4 illustrates different employment options for a package such as the one in FIG. 1.

As described in FIG. 4, the user device may consist in a syringe for injection or withdrawal 22 with a luer 23 for the opening of connector 16, or a similar syringe for injection or withdrawal 24 with a luer 25 and a luer-lock device 26, or a simple input or collection bag 27 with a connector 28 shaped to complement connector 16 (or otherwise connected to outflow tube 15 of bag 1), as well as a two-way flow-diverting tap 29 placed between connector 16 and a complementary connector 30 of a lower bag, and which may be coupled to a syringe for withdrawal and reconstitution.

This latter application is detailed in FIGS. 5-9, where items corresponding to those in FIGS. 1-4 are referenced with the same numbers.

Figure 5:
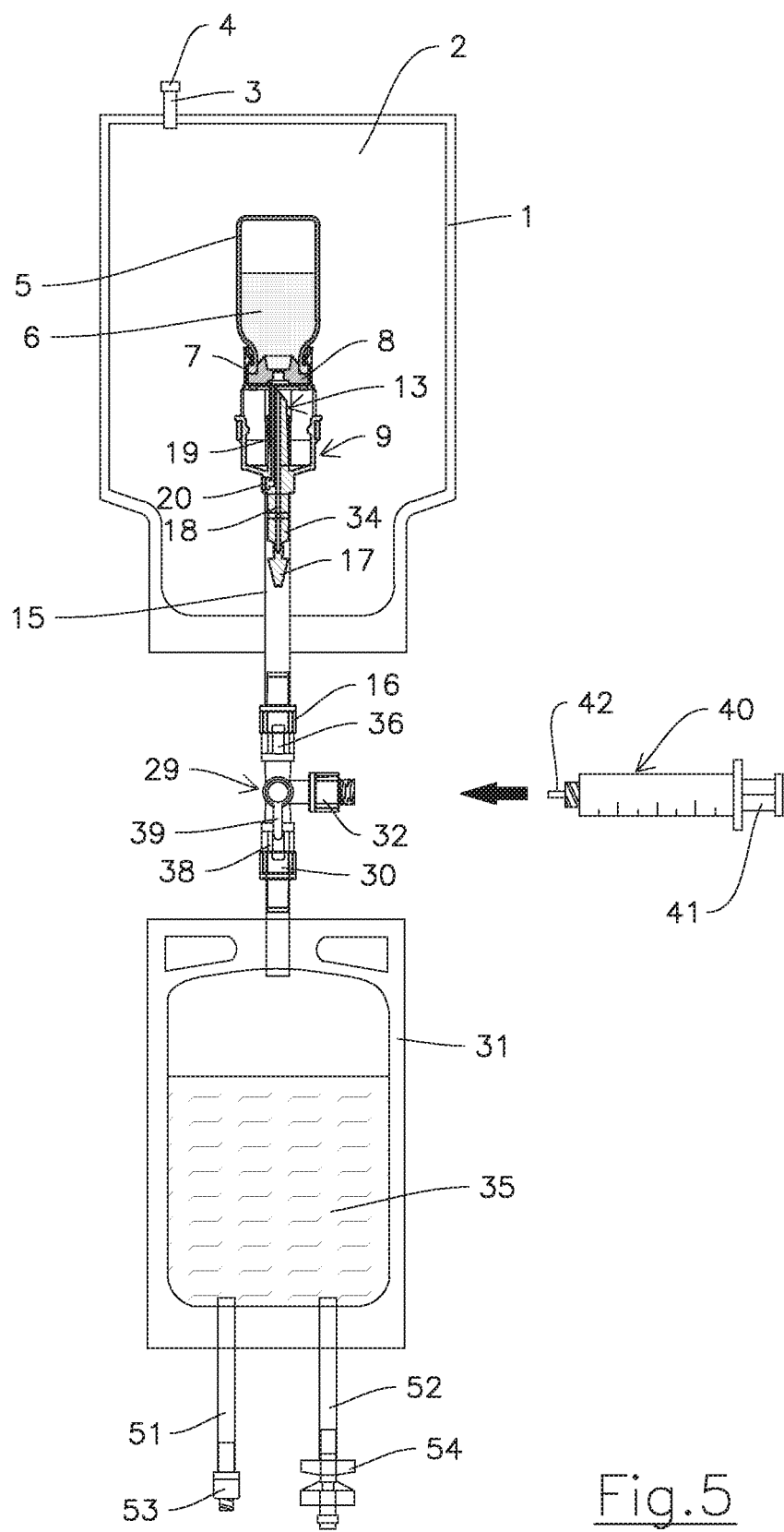
FIGS. 5-9 show in greater detail the processing sequence for the mixing of the substance contained in the bottle with the one contained in the lower bag by means of a two-way tap and a syringe.

As shown in FIG. 5, between the two bags 1 and 31—the former containing a medicinal or nutritional substance 6 and the latter filled with a suitable liquid diluent 35 (or other liquid substance that may be mixed with medicinal or nutritional substance 6) and equipped with an inlet tube 51 with a connector 53 and an outlet tube 52 with an openable cap 54—a two-way tap 29 is placed, which comprises three nozzles with a connector each (36, 38, 32), the first of which may be coupled to connector 16 of bag 1, the second to connector 30 of bag 31, while the third is normally sealed but may be opened and perforated with a syringe 40 with sliding plunger 41 and a luer 42 at the end. Tap 21 is adjustable into two positions by operating a rotating component 39. Connections between tap 29 and bags 1 and 31 may be permanent rather than through connectors 16, 36, and 30, 38.

In this case tap 29 is adjusted before use so as to inhibit any communications with lower bag 31, while tube 15 is closed with closure 17, as shown in FIG. 5.

Figure 6:
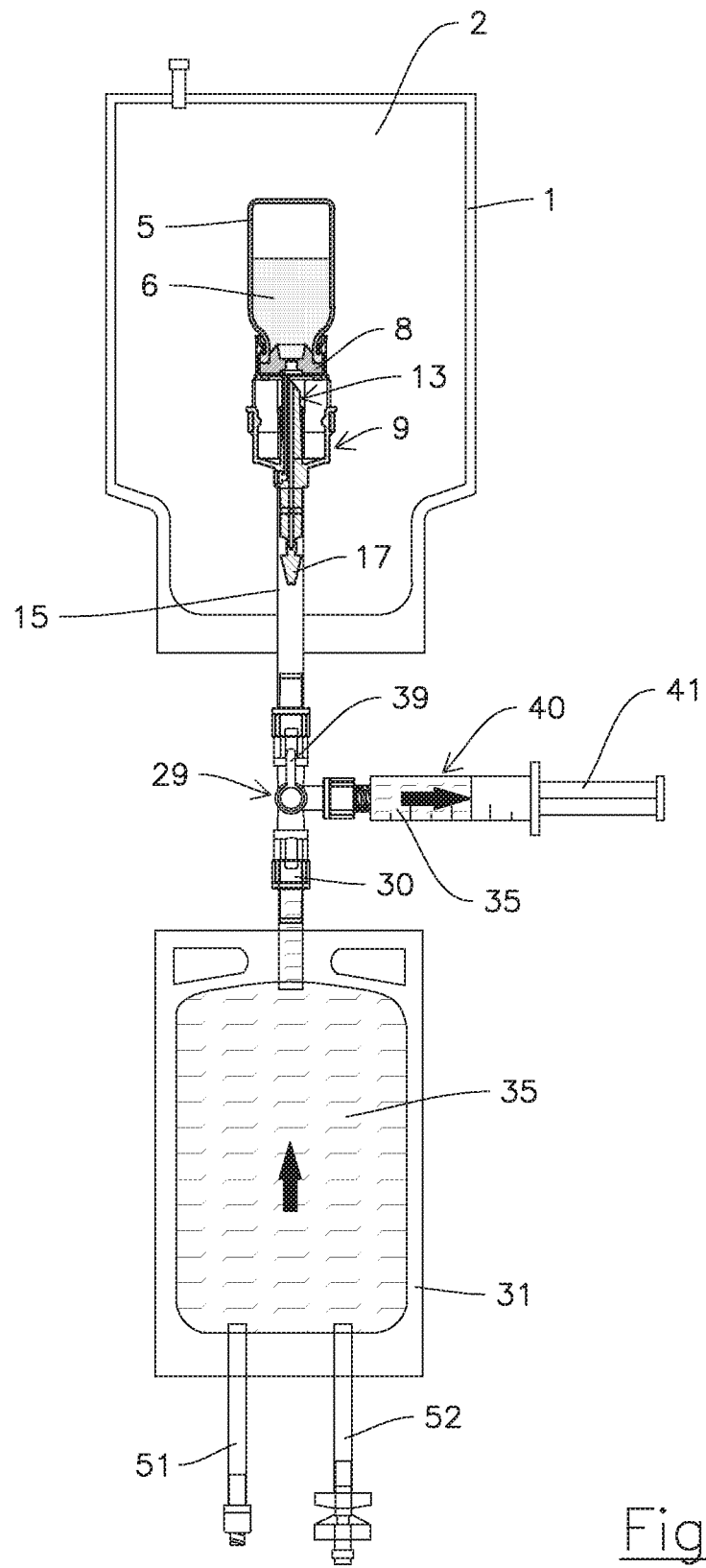

In order to mix a dosed quantity of pharmaceutical or nutritional substance 6 with diluent 35, syringe 40 with plunger 41 pushed all the way in as in FIG. 5 is connected to tap 29 by inserting luer 41 inside connector 32, then the rotating component 39 of tap 29 is turned into a position so as to inhibit communications with tube 15 and open connections to the inner chamber of bag 31; then, plunger 41 of the syringe is pulled backwards until a dosed quantity of diluent 35 is withdrawn from bag 31 (FIG. 6).

Figure 7:
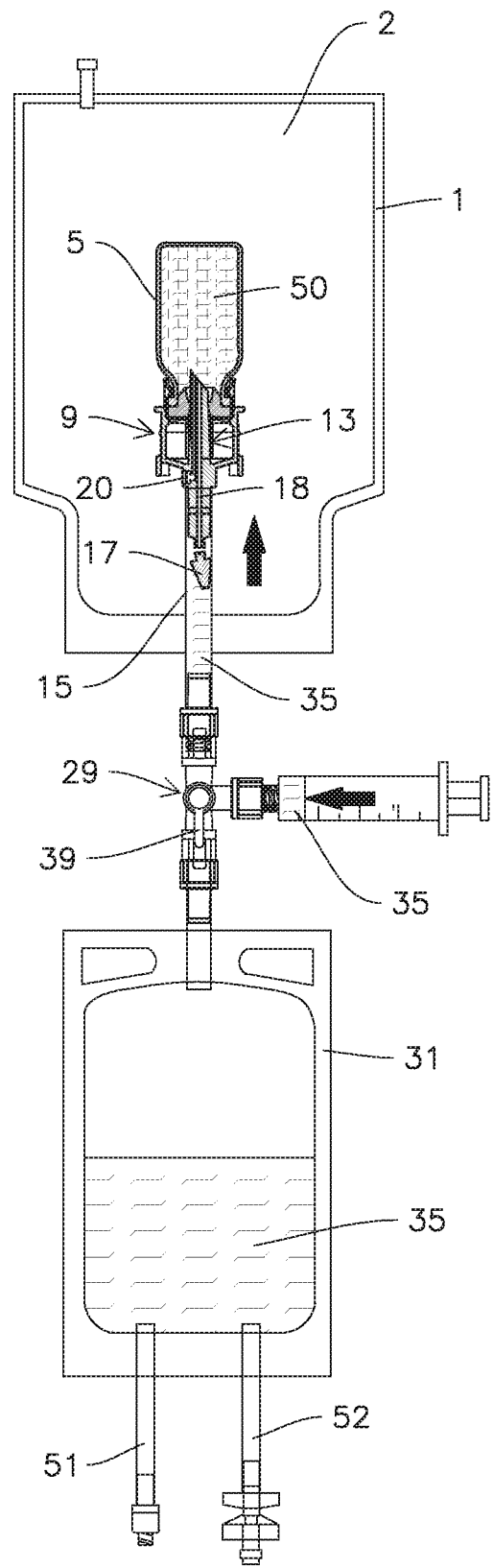

Tap 29 is then adjusted so as to stop communications with the inner chamber of bag 31, the frangible closure 17 is broken to open connections between internal channel 18 of needle 13 and tube 15, and bottle 5 is pushed downwards, thereby forcing the tip of needle 13 into cap 8 of bottle 5 (FIG. 7). Plunger 41 of syringe 40 is then pushed in in order to deliver the quantity of diluent withdrawn from bag 31 inside bottle 5, thus forming therein a mixture 50 of medicinal or nutritional substance 6 and diluent 35 (FIG. 7). At this stage, the air inside bottle 5 is forced to flow out of bottle 5 into inner chamber 2 of bag 1 through channel 19 and side opening 20. Hydrophobic filter 21 allows the passage of air while preventing substance 6 or mixture 50 from passing through.

Figure 8:
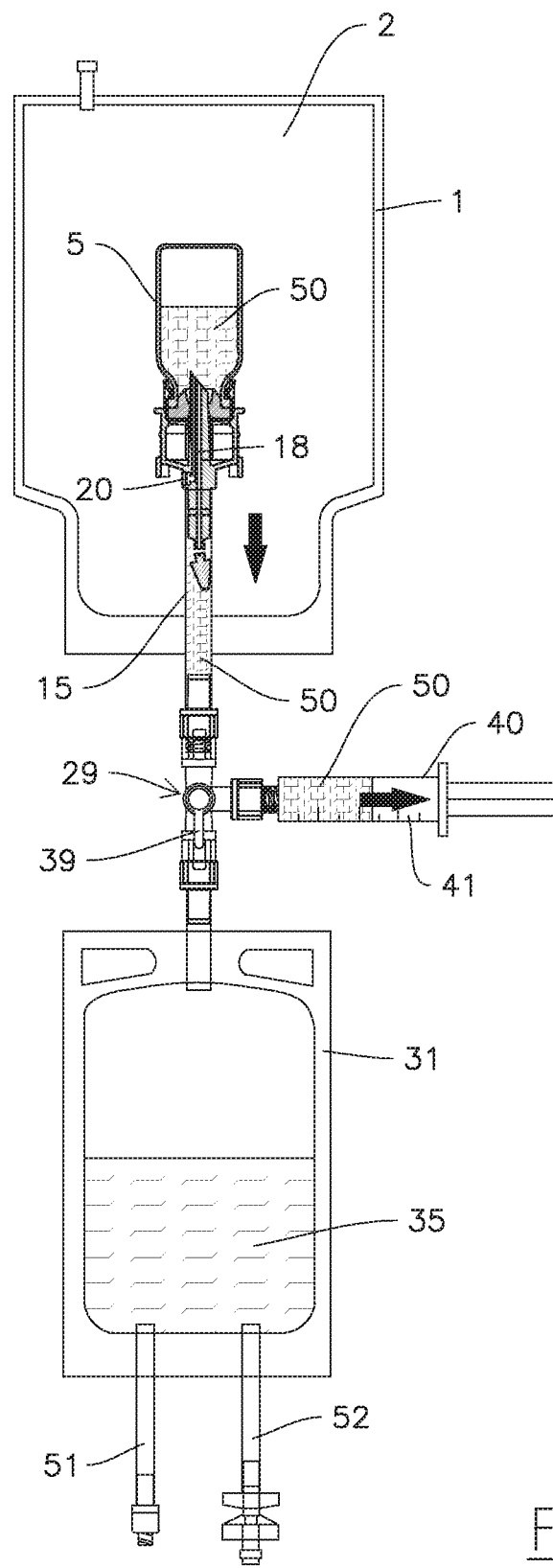

With tap 29 still set in the position described above, a dosed quantity of mixture 50 is then withdrawn from syringe 40 by pulling plunger 41 backwards, as illustrated in FIG. 8. The air previously forced into inner chamber 2 of bag 1 may flow back into bottle 5 through opening 20 with hydrophobic filter 21 and channel 18 of needle 13.

Figure 9:
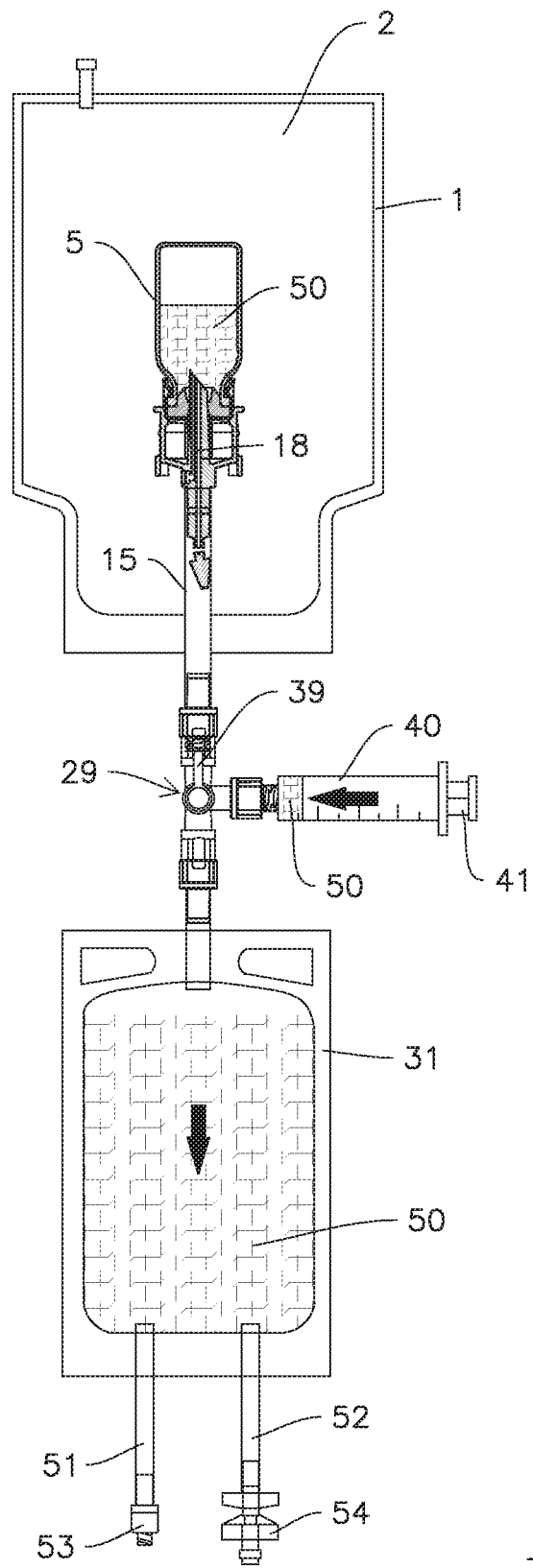

Tap 29 is then set back into a position of closure of tube 15 and opening of communications with the inner chamber of bag 31, and plunger 41 is pushed in to deliver the dosed quantity of mixture 50 previously withdrawn from bottle 5 into bag 31 (FIG. 9). Bag 31 is then ready for use.

The invention claimed is:

1. A package for administration of medicinal or nutritional substances, comprising:
an outer bag with a sterilized inner chamber,
a bottle of medicinal or nutritional substance set in an overturned position and disposed within the inner chamber of the outer bag, the bottle comprising a neck and a pierceable cap set in the neck,
a device configured to withdraw or reconstitute the substance contained in the bottle, the device is hooked to the neck of the bottle, and the device comprises a perforation needle configured to move in an axial direction relative to the bottle and perforate the cap of the bottle and a bottom shank extending from a base of the needle, and
an outflow tube hermetically receiving the bottom shank and extending out of the outer bag, the outflow tube comprising an openable closure element disposed in a passage of the outflow tube,
wherein said perforation needle comprises:
a first channel extending longitudinally through the perforation needle such that first channel establishes fluid communication between an interior of the bottle and the passage of the outflow tube when the perforation needle perforates the cap and the closure element is opened, and
a second channel extending from a side opening of the perforation needle to a tip of the perforation needle, wherein the side opening is disposed at the base of the needle above the bottom shank and opens directly into the inner chamber of the outer bag,
a hydrophobic filter disposed within the perforation needle at the side opening of the perforation needle and configured to allow only gaseous fluid to flow through the second channel such that gaseous fluid flows between the interior of the bottle and the inner chamber of the outer bag when the perforation needle perforates the cap,
wherein the device is configured to: (1) direct gaseous fluid to flow from the interior of the bottle to the inner chamber of the outer bag by permitting only gaseous fluid to flow through the second channel of the perforation needle when a liquid substance is flowing from the passage of the outflow tube to the interior of the bottle via the first channel, and (2) direct gaseous fluid to flow from the inner chamber of the outer bag to the interior of the bottle by permitting only gaseous fluid to flow through the second channel of the perforation needle when the liquid substance is flowing from the interior of the bottle to the passage of the outflow tube via the first channel.

2. The package according to claim 1, wherein the device comprises an upper body having flaps configured to be hooked to the neck of the bottle and a lower body slidably coupled to the upper body, the lower body comprises the perforation needle and the bottom shank, and the first channel extends in a longitudinal direction through the bottom shank, wherein the base of the needle extends below the upper body when the perforation needle is moved upward in the axial direction relative to the bottle and perforates the cap of the bottle.

3. The package according to claim 1, wherein the outflow tube includes an end connector disposed at an end of the outflow tube and configured to open and close the end of the outflow tube.

4. The package according to claim 3, wherein the end connector is configured to be coupled to an opening of a syringe.

5. The package according to claim 1, wherein the outer bag is made of a flexible material.

6. The package according to claim 1, wherein the outer bag comprises a tube with an airtight connector configured to open and close to introduce a mixture of ozone or a sterilizing gas into the inner chamber of the outer bag.

7. The package according to claim 1, comprising:
a second bag positioned below said outer bag and configured to contain the liquid substance to be mixed with said medicinal or nutritional substance, and
a two-way tap disposed between the outer bag and the second bag, the two-way tap comprising a side connector configured to be coupled to an opening of a syringe with a sliding plunger, wherein the two-way tap is configured to be adjusted between a first position inhibiting fluid communication between the side connector and the second bag, and a second position inhibiting fluid communication between the side connector and the outflow tube of the outer bag.

8. The package according to claim 7, wherein the two-way tap comprises a first connector secured to an end connector of the outflow tube of the outer bag and a second connector secured to an end connector of a second outflow tube of the second bag.

9. The package according to claim 7, wherein the two-way tap is permanently secured to the outflow tube of the outer bag and a second outflow tube of the second bag.

10. The package according to claim 1, comprising:
a collection bag positioned below the outer bag and in fluid communication with the outer bag.

* * * * *